United States Patent [19]
Tatsumi

[11] Patent Number: 5,240,578
[45] Date of Patent: Aug. 31, 1993

[54] CAPILLARY ELECTROPHORESIS SYSTEM AND METHOD

[75] Inventor: Nobuyuki Tatsumi, Kyoto, Japan

[73] Assignee: Shimadzu Corporation, Kyoto, Japan

[21] Appl. No.: 938,695

[22] Filed: Sep. 1, 1992

[30] Foreign Application Priority Data

Sep. 24, 1991 [JP] Japan ................... 3-242209

[51] Int. Cl.$^5$ ................... G01N 27/26; G01N 27/447; B01D 57/02
[52] U.S. Cl. ................... 204/180.1; 204/299 R
[58] Field of Search ................... 204/299 R, 180.1

[56] References Cited

FOREIGN PATENT DOCUMENTS 329341 8/1989 European Pat. Off. ........ 204/299 R
339781 11/1989 European Pat. Off. ........ 204/299 R
395796 11/1990 European Pat. Off. ........ 204/299 R

OTHER PUBLICATIONS

Stephen E. Moring et al "Analytical Aspects of a Automated Capillary Electrophoresis System" LC-GC, vol. 1, No. 1 (1990) 34-46.

G. Schomburg et al "Construction, Evaluation, and Analytical Operation of a Modular Capillary Electrophoresis Instrument" Chromatographia vol. 30, No. 1/2 (Jul. 1990) 7-15.

*Primary Examiner*—John Niebling
*Assistant Examiner*—John S. Starsiak, Jr.
*Attorney, Agent, or Firm*—Heller, Ehrman, White & McAuliffe

[57] ABSTRACT

A capillary electrophoresis system has a sample tube from which a sample is injected into a capillary tube by introducing a gas thereinto through an on-off valve. In order to maintain its internal pressure constantly at a target level, the pressure inside the sample tube is monitored after the valve is closed, and the period of time during which the valve is opened is adjusted according to the difference between the maximum level, to which the internal pressure reaches, and an upper limit value predefined above the target level.

3 Claims, 4 Drawing Sheets

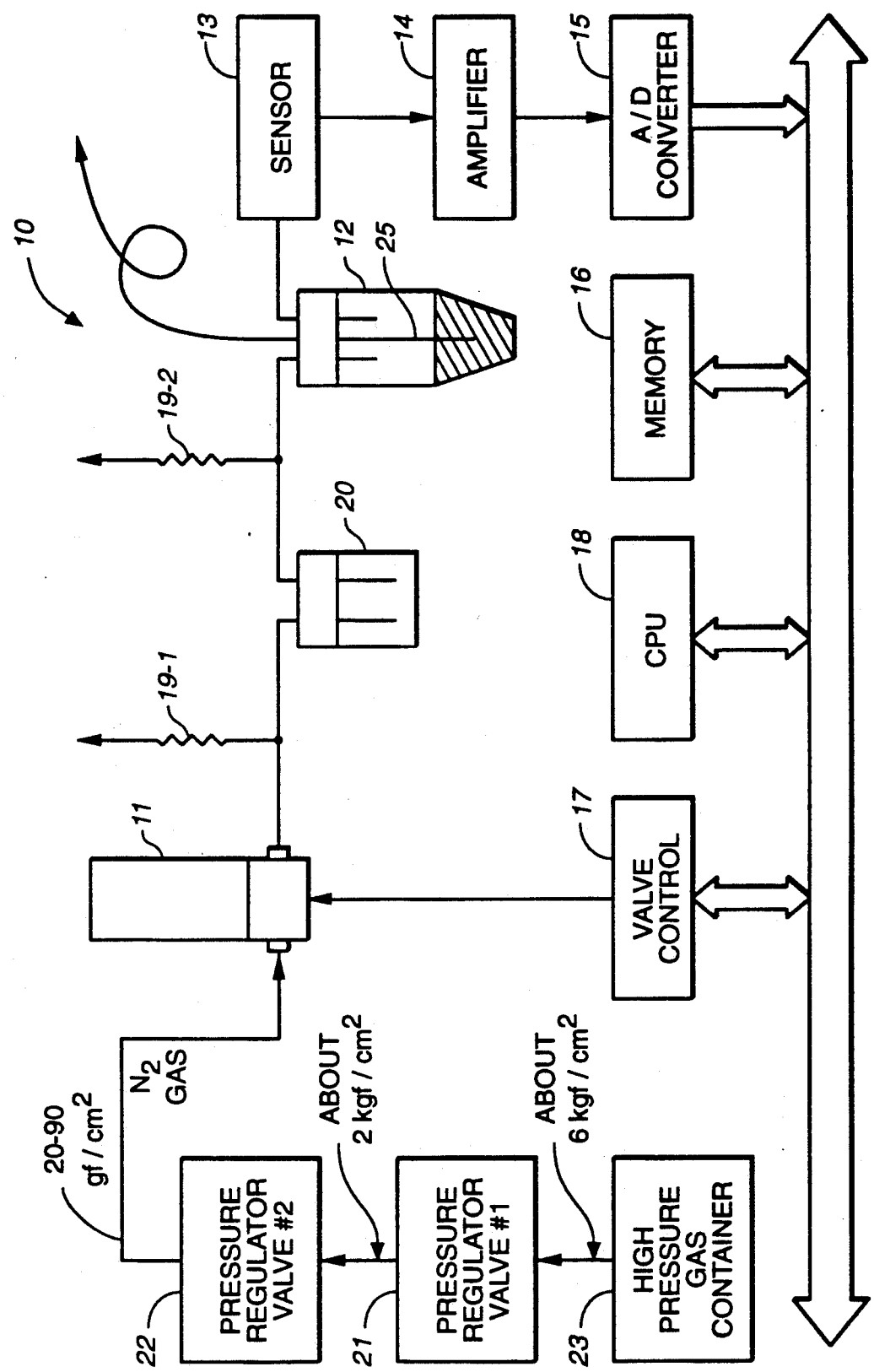
FIG._1

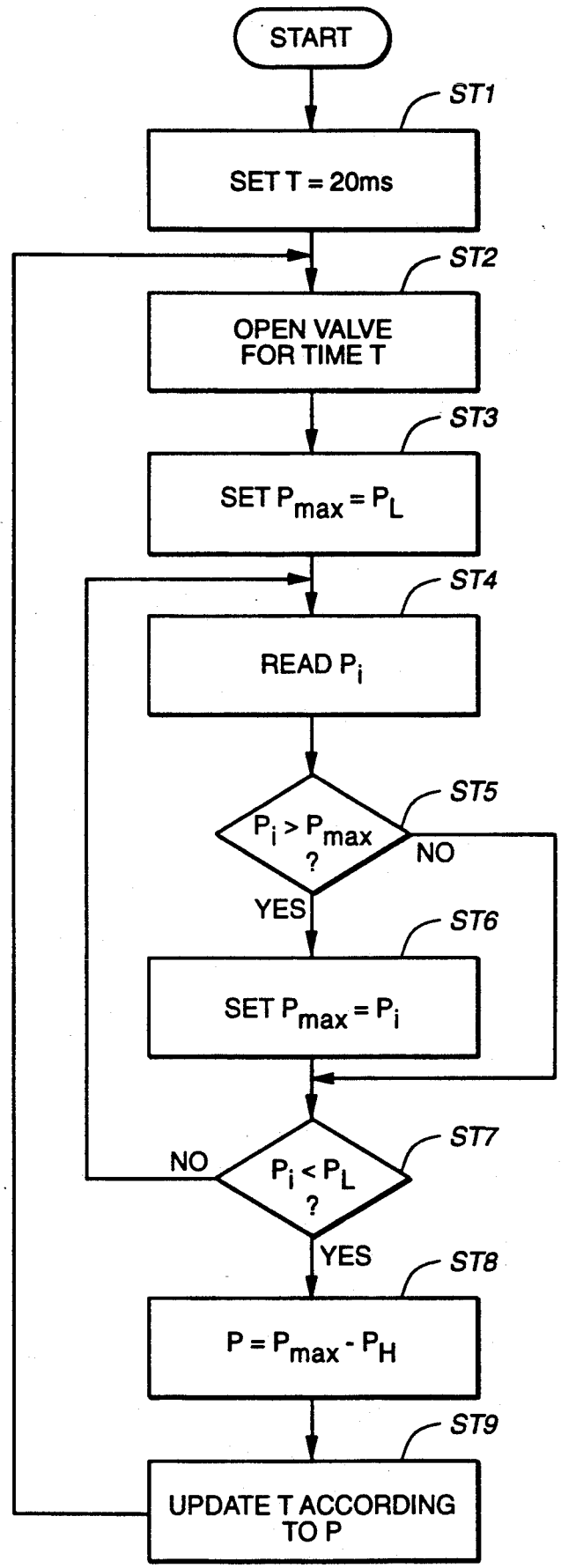
FIG._2

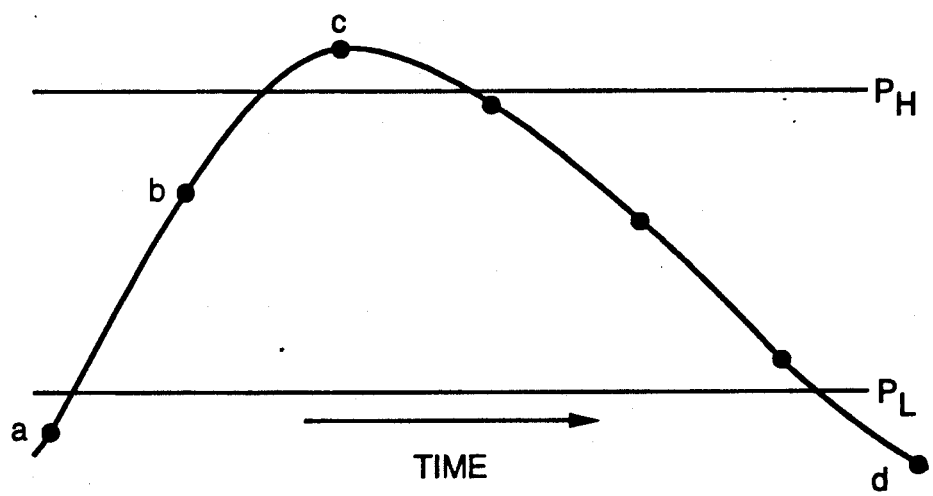
FIG._3

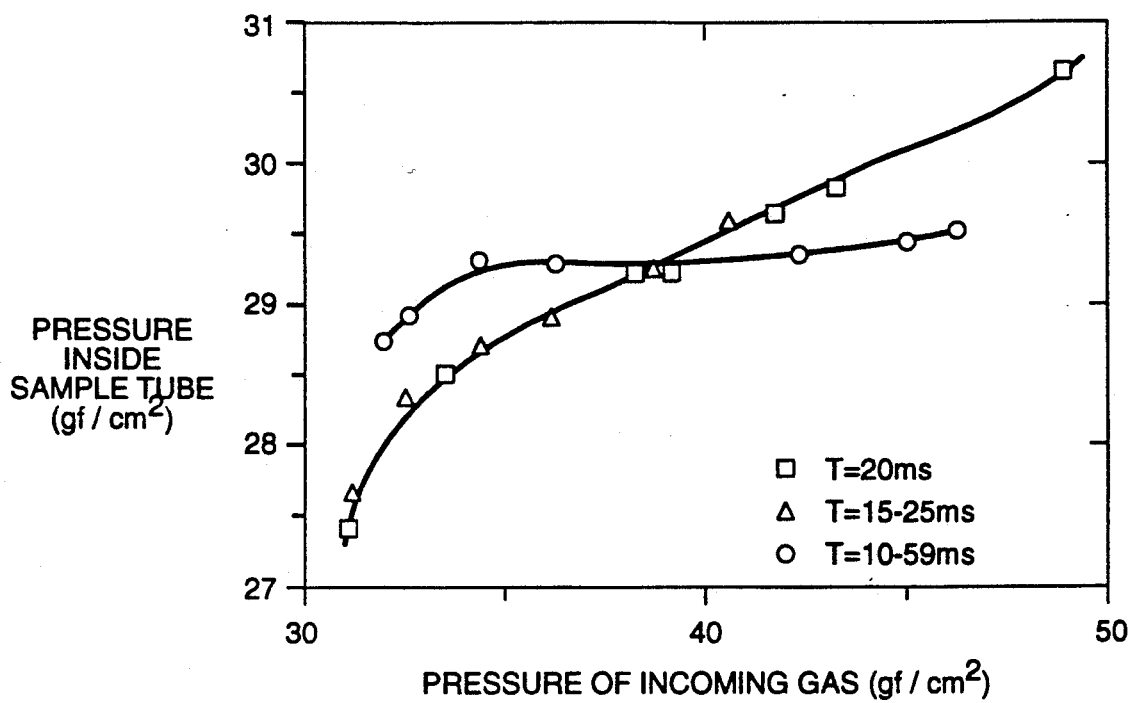
FIG._4
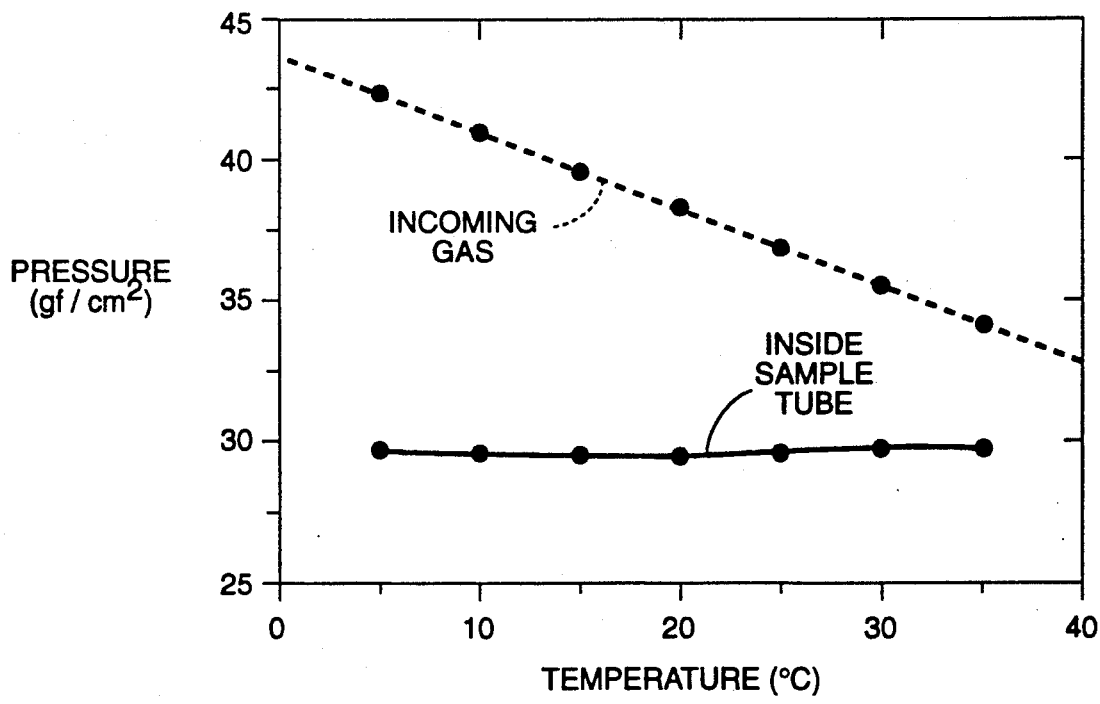
FIG._5

CAPILLARY ELECTROPHORESIS SYSTEM AND METHOD

BACKGROUND OF THE INVENTION

This invention relates to a capillary electrophoresis system and a method of controlling the gas pressure inside a sample tube thereof as a sample is injected therefrom into a capillary tube.

Methods of injecting a sample into a capillary tube include the so-called syphon method, potential difference method and compression method. Of the above, the compression method is one whereby the sample is preliminarily placed inside a sample tube and the gas pressure therein is increased by introducing high-pressure nitrogen gas or the like thereinto. If such a gas is made to pass through a solenoid valve on its way into the sample tube, the gas pressure inside the sample tube can be controlled by opening and closing this valve. In order to accurately inject a specified amount of the sample from the sample tube into the capillary tube in this manner, it is necessary to keep the gas pressure inside the sample tube at a specified constant level.

One method of controlling the gas pressure for such a purpose is to preliminarily set an upper limit value (such as 51 gf/cm$^2$) and a lower limit value (such as 49 gf/cm$^2$) for a given target pressure level (such as 50 gf/cm$^2$) and to close the valve if the pressure inside the sample tube exceeds the upper limit value, while opening the valve if the pressure is below the lower limit value. Because of the finite volume of the gas flow system, however, there is a time lag between the opening or closing of the valve and the resultant change in the gas pressure. The gas pressure may even keep oscillating beyond and over the specified upper and lower limit values. Since the pressure inside the sample tube is generally low (much lower than 100 gf/cm$^2$), furthermore, it is easily affected by changes in the ambient temperature or even a small leak in the gas flow system. As a result, the gas pressure may change significantly and the variations of its maxima and minima may grow larger. In such a situation, it is not possible to set the gas pressure accurately to a specified level. Although this time lag between the opening and closing of the valve and the pressure change can be reduced by making the total volume of the gas flow system smaller, the changes in pressure will become too large making it impossible to keep the pressure constant inside the sample tube.

It is therefore an object of the present invention to provide a capillary electrophoresis system and a method by which gas pressure can be accurately controlled.

SUMMARY OF THE INVENTION

A capillary electrophoresis system embodying the present invention, with which the above and other objects can be accomplished, may be characterized as comprising an on-off valve for opening and closing a gas flow route, a sample tube from which a sample is injected into a capillary tube by the pressure of a gas, the flow of which is controlled by this valve, a sensor for measuring the gas pressure inside this sample tube, a memory device for receiving outputs from this sensor and storing the maximum value of pressure after the valve is closed until the gas pressure drops, and a control device which, when the output from the sensor becomes smaller than a preliminarily set lower limit value after the valve is closed, keeps the valve open for a period of time determined from the difference between the maximum value stored in the memory device and a preliminarily set upper limit value.

With a system thus structured, the valve is opened and closed, and the sample inside the sample tube is injected into the capillary tube by the pressure of the gas of which the flow is controlled by the operation of the valve. The sensor is adapted to measure the gas pressure inside the sample tube and to output signals indicative of the measured pressure value. The memory device receives these signals from the sensor and stores the maximum pressure value after the valve is closed, causing the pressure to rise inside the sample tube 12, until the gas pressure drops to a certain lower level. If the output from the sensor becomes lower than a preliminarily set lower limit value, the control device causes the valve to open for a time period (hereinafter referred to as the open period) determined from the difference between the maximum pressure value stored by the memory device and a preliminarily set upper limit value. The open period is made shorter if the maximum pressure value is much greater than the upper limit value. The open period is made longer if the maximum pressure value is much below the upper limit value.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a block diagram of a capillary electrophoresis system embodying the present invention;

FIG. 2 is a flow chart for showing the operation of the system of FIG. 1;

FIG. 3 is a graph for schematically showing the change in gas pressure controlled by the system of FIG. 1;

FIG. 4 is a graph for showing the effect of the pressure of incoming gas on the average pressure inside the sample tube; and FIG. 5 is a graph for showing the effect of temperature on the average pressure inside the sample tube and the pressure of incoming gas.

DETAILED DESCRIPTION OF THE INVENTION

As schematically shown in FIG. 1, a capillary electrophoresis system 10 embodying the present invention is comprised of a solenoid valve 11 serving as an on-off valve for opening and closing a flow route of nitrogen gas, a sample tube 12 for injecting a sample into a capillary tube 25, a sensor 13 for measuring the pressure inside the sample tube 12, an amplifier 14 for amplifying output signals from the sensor 13, an analog-to-digital (A/D) converter 15 for converting outputs from the amplifier 14 into digital signals, a memory device 16 for storing data from the A/D converter 15, a valve control unit 17 for controlling the opening and closing operations of the solenoid valve 11 and a central processing unit (CPU) 18 for controlling the entire operation of the system 10. The system 10 further includes a high-pressure gas container 23, a first pressure regulator valve 21 for regulating the pressure of about 6 kgf/cm$^2$ of the gas from the container 23 to a level of about 2 kgf/cm$^2$ and a second pressure regulator valve 22 for regulating the gas pressure from about 2 kgf/cm$^2$ to a level of about 20-90 gf/cm². The gas flow route between the solenoid valve 11 and the sample tube 12 is provided with resistance tubes 19-1 and 19-2 and a damper 20 of known kinds for suppressing sudden changes of the gas pressure therein.

A method of operating the system 10 will be described next with reference to the flow chart of FIG. 2 and the graph of FIG. 3 for a situation where the target gas pressure is 29.3 gf/cm², and the upper limit value $P_H$ and the lower limit value $P_L$ have been set respectively to 30.1 gf/cm² and 28.9 gf/cm². The incoming pressure of the nitrogen gas to be controlled by the solenoid valve 11 will be assumed to be about 40±5 gf/cm².

By way of initialization, the CPU 18 sets the open period T of the solenoid valve 11, say, to 20ms (ST1). When the pressure inside the sample tube 12 is below the lower limit value (at Point a in FIG. 3), the valve control unit 17 causes the solenoid valve 11 to open for a duration of time given by T (ST2). The CPU 18 also sets the value of a dummy variable $P_{max}$ equal to the lower limit value $P_L$. This dummy variable $P_{max}$ is for the purpose of determining the maximum pressure in the sample tube 12 after the solenoid valve 11 is closed. Thereafter, pressure values $P_i$ inside the sample tube 12, obtained from the output signals from the sensor 13, are received successively by the CPU 18 at a constant time interval (ST4), as indicated by Points a, b, c,... d in FIG. 3). Let us assume, for convenience, that this constant time interval is 20ms. In other words, the solenoid valve 11, initially opened at Point a (ST2), will close at Point b, but since the effect of opening and closing the solenoid valve 11 is communicated to the sample tube 12 with a finite time delay, the pressure inside the sample tube 12 keeps rising for some time even after the solenoid valve 11 is closed (at Point b). It may start to drop, say, after about 40ms (from Point a). Meanwhile, each time a new pressure value $P_i$ is received from the sensor 13 (at Points b, c,...), it is compared with the current value of the dummy variable $P_{max}$ (ST5) and, if $P_i$ is greater than $P_{max}$, the value Of the dummy variable $P_{max}$ is updated to $P_i$ (ST6).

The pressure value $P_i$ is also compared with the preliminarily set lower limit value $P_L$ (ST7). The steps ST4 through ST6 are repeated until $P_i$ becomes smaller than $P_L$. By the time the pressure $P_i$ inside the sample tube 12 finally becomes smaller than the lower limit value $P_L$ (Point d), the value of the dummy variable $P_{max}$ should be indicating the maximum value of the pressure level outputted from the sensor 13. The CPU 18 then calculates the difference $P=P_{max}-P_H$ between this maximum pressure value and the preliminarily set upper limit value (ST8). The value of the open period T for the solenoid valve 11 is updated according to this difference value P (ST9), and the solenoid valve 11 is opened again (ST2), but this time for a different time period given by the updated value of T. Stated broadly, the open period T of the solenoid valve 11 is shortened if $P_{max}>P_H$, and it is made longer if $P_{max}<P_H$. Thereafter, the steps ST2 through ST9 are repeated. In each cycle, the pressure inside the sample tube 12 will change with time more or less as shown schematically in FIG. 3, rising to a certain maximum value and then gradually falling below the level of the lower limit value $P_L$ to cause the solenoid valve 11 to open again. Thus, the open period T of the solenoid valve 11 is updated after each cycle.

In an actual operation, however, the open period T cannot be shorter than the response time of the solenoid valve 11 (usually in the range of about 6ms-10ms). For this reason, a lower limit value is preliminarily set for the open period T such that even if the calculated value of updated open period is less than such a preliminarily set lower limit value, the solenoid valve 11 is opened for the lower limit value. On the other hand, if the calculated value of updated open period becomes too large, it is likely that there is a leak in the system. For this reason, a maximum value is also preliminarily set such that the open period T will not be made any larger than such a maximum value.

A method of updating the open period T on the basis of the difference value P may be described, for example, as replacing the current value of T by a new value given by $T(1-\alpha P/P_H)$ where $\alpha$ is a proportionality constant to be empirically determined. For example, in experiments in which the pressure of the gas passing through the solenoid valve 11 of FIG. 1 was varied between 30 and 50 gf/cm₂, with the target pressure, upper limit and lower limit values given as above, it was observed that the pressure inside the sample tube 12 could be kept uniform if the open period T was changed by 1% when $P/P_H=1/1000$. In this situation, a preferred value of $\alpha$ will be about 10. FIG. 4 shows the effect of the pressure of the incoming gas on the average pressure inside the sample tube 12. It shows that the average pressure inside the sample tube 12 can be kept reasonably constant near the target value of 29.3 gf/cm² if the open period T is allowed to change in a wider range of 10-59ms (indicated by circles) than if it is kept unchanged at 20ms (indicated by squares) or is allowed to change in a narrower range of 15-25ms (indicated by triangles).

FIG. 5 shows the effect of temperature on the average pressure inside the sample tube 12 and the pressure of the incoming gas as the open period time T was changed as explained above. This also shows that the average pressure inside the sample tube 12 can be kept nearly constant at the target value independent of the ambient temperature, although the pressure of the gas inside the gas transportation route varies rather significantly (35-45gf/cm²) as the temperature was changed from 5° C. to 35° C.

In actual instances of sample injection, the system 10 is controlled in such a way that the waveform (as shown in FIG. 3) will be substantially uniform from when it reaches the lower limit value to when it reaches the upper limit value. Thus, it is possible not only to carry out injection with improved repeatability by controlling the open period of the solenoid valve but also to maintain a linear relationship between the time of applying pressure (that is, the open period) and the amount of injected gas. Another advantage of the method according to the present invention is that the pressure of the incoming gas (that is, the output from the pressure regulator valves) need not be accurately controlled because its variations are restrained according to the present invention by the changes in the open period of the solenoid valve.

The invention has been described above by way of only one embodiment, but this embodiment is not intended to limit the scope of the invention. Many modifications and variations are conceivable within the scope of the invention. Such modifications and variations that may be apparent to a person skilled in the art are intended to be within the scope of the invention.

What is claimed is:
1. A capillary electrophoresis system comprising:

an on-off valve for opening and closing a gas flow route;

a sample tube for injecting a sample into a capillary tube by the pressure of gas introduced thereinto through said on-off valve;

a sensor for measuring the pressure inside said sample tube;

a memory device for receiving output signals from said sensor and storing therein as maximum pressure value the largest pressure measured by said sensor from when said on-off valve is closed and until the pressure as measured by said sensor drops; and a control device adapted to open said on-off valve for a time period determined by the difference between said maximum pressure value stored in said memory device and a preliminarily set upper limit value when the pressure as measured by said sensor becomes lower than a preliminarily set lower limit value after said on-off valve is closed.

2. A method of operating a capillary electrophoresis system, said system including an on-off valve for opening and closing a gas flow route, and a sample tube for injecting a sample into a capillary tube by the pressure of gas introduced thereinto through said on-off valve, said method comprising the steps of:

(a) selecting a target pressure value, an upper limit value greater than said target pressure value and a lower limit value lower than said target pressure value;

(b) opening said on-off valve for a predetermined open period of time to thereby introduce a gas into said sample tube when the pressure inside said sample tube is below said lower limit value;

(c) monitoring changes in the pressure inside said sample tube to thereby identify a maximum pressure value after said on-off valve is closed;

(d) determining the difference between said maximum pressure value and said upper limit value;

(e) changing said predetermined open period of time by a correction amount which is determined by said difference; and (f) repeating said steps (b)–(e).

3. The method of claim 2 wherein said correction amount varies proportionally with said difference.

* * * * *

UNITED STATES PATENT AND TRADEMARK OFFICE
CERTIFICATE OF CORRECTION

PATENT NO. : 5,240,578
DATED : August 31, 1993
INVENTOR(S) : Nobuyuki Tatsumi, et al.

It is certified that error appears in the above-indentified patent and that said Letters Patent is hereby corrected as shown below:

Column 3, line 10, "PH" should be --$P_H$--

Column 3, line 46, "PL" should be --$P_L$--

Column 3, line 51, "PH" should be --$P_H$--

Signed and Sealed this

Fifteenth Day of March, 1994

*Attest:*

BRUCE LEHMAN

*Attesting Officer*   *Commissioner of Patents and Trademarks*